United States Patent [19]

Ryerson

[11] 4,203,946
[45] May 20, 1980

[54] OZONE DETECTING ELEMENT

[75] Inventor: Joseph L. Ryerson, Holland Patent, N.Y.

[73] Assignee: Energy for Independence, Inc., Holland Patent, N.Y.

[21] Appl. No.: 888,228

[22] Filed: Mar. 20, 1978

[51] Int. Cl.² .................... G01N 27/04; H01C 7/00
[52] U.S. Cl. ............................................ 422/98; 422/90;
23/232 E; 73/27 R; 324/71 SN; 338/34
[58] Field of Search ................................ 422/90, 98, 97;
23/232 E; 338/34; 324/71 SN; 73/27

[56] References Cited

U.S. PATENT DOCUMENTS

| | | | |
|---|---|---|---|
| 3,611,243 | 10/1971 | Hardtl | 338/34 |
| 3,625,756 | 12/1971 | Taguchi | 338/34 |
| 3,695,848 | 10/1972 | Taguchi | 324/71 SN |
| 3,699,803 | 10/1972 | Sumi et al. | 324/71 SN |
| 3,778,229 | 12/1973 | Webster et al. | 422/98 |
| 4,001,756 | 1/1977 | Heijne | 338/34 |
| 4,039,941 | 8/1977 | Morrison | 422/98 |
| 4,045,178 | 8/1977 | Okinaka et al. | 422/98 |

Primary Examiner—R. E. Serwin
Attorney, Agent, or Firm—Bruns & Jenney

[57] ABSTRACT

A detecting element for sensing the presence of higher than normal concentrations of ozone in air at ambient temperatures and pressures. The element is formed of a "lower" oxide of a semiconductor having a variable valence. In the presence of ozone, two free electrons in the conductive band of the semiconductor combine with dissociated atomic oxygen to form a "higher" oxide of the semiconductor thereby changing the conductivity of the element. At least two electrodes are placed in spaced apart contact with the element to permit a current to be passed therethrough whereby the change in conductivity can be discerned.

12 Claims, 2 Drawing Figures

OZONE DETECTING ELEMENT

BACKGROUND OF THE INVENTION

This invention relates to the detection of ozone and, in particular, to the detection of slightly higher than normal concentrations of ozone in air at ambient temperatures and pressures.

More specifically, this invention relates to the use of a semiconductor to detect the presence of ozone in air. Gas detectors formed of porous N-type semiconductors have been used for quite some time to detect the presence of reducing agents, such as carbon monoxide or the like. The typical application of this type of device has been in fire warning systems. In operation, a porous sensor adsorbs the reducing agents or gases present in smoke whereby a reduction reaction takes place causing the conductivity of the sensing element to increase and thereby trigger an alarm circuit. This type of semiconductor element, and the method of manufacturing the same, is disclosed in a series of United States patents to Taguchi which include: U.S. Pat. Nos. 3,625,756, 3,631,436, 3,644,795, 3,676,820, 3,695,848, 3,732,519, 3,835,529, 3,900,815.

As disclosed by Taguchi, the semiconductor sensing element is generally formed of a high valance oxide capable of giving up an oxygen molecule to the adsorbed reducing agent. At the same time, two valance electrons are released to the conduction band of the element thus rendering it more conductive. Because of the amount of energy needed to produce the reaction is relatively high, the element is normally provided with a heater adapted to maintain the sensor at an elevated operating temperature. In fact, the high valence oxide semiconductor's sensitivity to a reducing agent, if dicernible at all, at room temperatures is weak and unpredictable.

Accordingly, it has heretofore been thought that oxide type semiconductors were suitable only for detecting the presence of certain reducing agents at elevated temperatures. However, as will be explained in greater detail below, this type of detector can be adapted to sense the presence of slightly higher than normal concentrations of ozone in air at ambient temperatures and pressures. The existence of small amounts of ozone in air is deemed to constitute an environmental hazard particular to those suffering from cardia-vascular ailments.

One area where overexposure to ozone is of primary concern is in the field of aviation where high flying aircraft are capable of remaining in the earth's ozone layer for relatively long periods of time. As the exact location of this layer is constantly in response to many factors, the pilot of an aircraft has no existing way of detecting the danger. As a consequence, cabin air which is drawn from surrounding outside air, can become contaminated with high levels of ozone thereby overexposing the passengers and crew for what could be extended periods of time. Presently, equipment for quickly and rapidly detecting this hazardous situation, while at the same time withstanding the rigors of high altitude flying, is not available.

SUMMARY OF THE INVENTION

It is therefore an object of this invention to improve equipment for sensing greater than normal concentrations of ozone in air.

Another object of the present invention is to provide a solid state ozone detecting element.

A further object of the present invention is to quickly and accurately detect the presence of slightly higher than normal levels of ozone in air.

A still further object of the present invention is to provide a solid state ozone detecting element that is capable of operating at ambient temperatures and pressures.

Yet another object of this invention is to improve the state of environmental protection by allowing for rapid detection of the presence of ozone in environmental air.

These and other objects of the present invention are attained by means of a solid state sensing element that includes a generally porous body formed of a lower oxide semiconductor material having at least a next higher oxide state which, in the presence of ozone at ambient conditions, reacts with dissociated atomic oxygen and free electrons in the conduction band to form a higher oxide of the semiconductor whereby the conductivity of the element is immediately and dicernibly changed.

BRIEF DESCRIPTION OF THE DRAWINGS

For a better understanding of these and other objects of the present invention, reference is had to the following detailed description of the invention which is to be read in conjunction with the following drawings, wherein.

DESCRIPTION OF THE INVENTION

Figure 1:
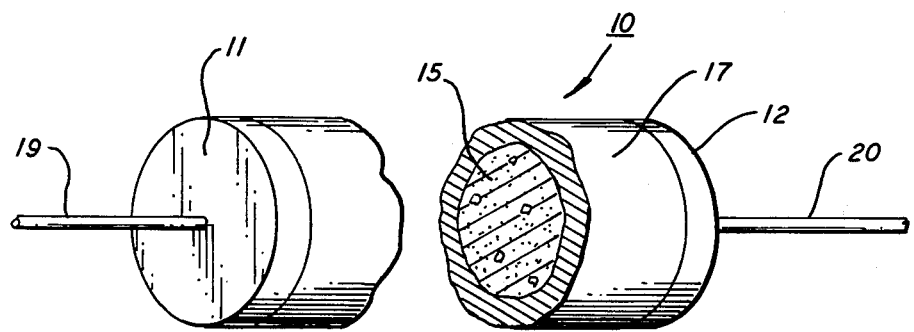
FIG. 1 is a perspective view with portions broken away showing a detecting element embodying the teachings of the present invention.

In the main embodiment of the invention illustrated in FIG. 1, there is shown a detecting element containing a variable valence oxide semiconductor. In this particular application, the element is formed of a low valence oxide of tin (stannous oxide) to provide a device that is capable of sensing the presence of slightly higher than normal concentrations of ozone in air at ambient temperatures and pressures. Although tin is disclosed as a preferred material, it should become clear from the disclosure below that a wide range of oxides exhibiting more than one valence state can be similarly employed. As is conventional, the term "low valence oxide" or "lower oxide" is herein used to define a variable valence oxide that has the ability to combine or react with oxygen to form a higher valence oxide or "higher oxide".

The body of the semiconductor is formed to supply a generally porous structure that is capable of adsorption ozone found in ambient air. The ozone is acted upon by the free electrons contained in the conduction band of the semiconductor to dissociate the ozone into atomic oxygen and molecular oxygen as follows:

$$O_3 \rightarrow O + O_2$$

Although the entire reaction that takes place is believed to be rather complex, the dissociated atomic oxygen and two free electrons contained in the conduction band now combine with the lower oxide starting material, which in the main embodiment is stannous oxide, to produce the next higher valence oxide, stannic oxide, as follows:

$$SnO + O + 2e^- \rightarrow SnO_2$$

As can be seen, the formerly free electrons are passed into the semiconductors valence band and are no longer available to aid in the conduction of electrical current through the element. In the case of an N-type material, such as stannous oxide, the conductivity of the element is thus reduced. Tests conducted on this type of detector have shown that the above noted reaction is readily carried out to completion at room temperatures and pressures without adding energy to the system.

The stannous oxide detector, as well as other lower oxide detectors, can also be conveniently restored to their original or normal sensing condition by purging excess oxygen therefrom using a simple thermal technique. During purging the higher valence stannic oxide is quickly reduced to stannous oxide by raising the temperature of the element to about 200° C. whereby the following reaction takes place:

$$SnO_2 - 2e^- \rightarrow SnO + \tfrac{1}{2}O_2$$

By heating the detecting element as noted, the two captured electrons are returned to the conduction band as free electrons and the molecular oxygen released or driven off as a gas.

An added advantage of utilizing a thermal purge resides in the fact that any moisture present, generally caused by high humidity, which could adversely affect the operation of the element, is also driven off at the purging temperature. As a result, the purged element is restored to an optimum sensing condition. Successful purging is ordinarily accomplished in five minutes or less at the temperature noted.

As noted above, as in the case of all N-type semi-conductors, free electrons are normally retained in the conduction band of the element. However, with the adsorption and dissociation of ozone, these normally free electrons are brought into the valence band to satisfy the higher oxide combination and are therefore made unavailable in the conducting of electrical energy through the element. As a consequence the conductivity of the element is reduced. Tests performed in regard to SnO and CO elements show that a dicernible reduction in conductivity is produced almost immediately when the material is exposed to air containing only slightly higher than normal concentrations of ozone. Normal concentrations of ozone in air are deemed to be about 15 parts per billion. The conductivity of other variable valance oxide semiconductors, such as FeO, $V_2O_3$, $WO_2$ and MnO, is similarly reduced upon exposure to small amounts of ozone in air.

The body of the sensing element can also be formed of a P-type material using such materials as CoO, $MoO_2$ and NiO. The P-type element contains electron "holes" in its conductive band and exhibits relatively high conductivity when the holes are unsatisfied by free electrons. In the present application, the dissociation of ozone causes electrons to be pulled out of the conduction band, where they are used to supply satisfied hole pairs, thus rendering the element more conductive. By the same token, upon being purged, the element will return or be restored to its normally more resistive state.

Referring now more specifically to FIG. 1, there is shown one form of the invention wherein a detector 10 contains a pair of circular conductive electrodes 11,12 that are supported in spaced apart relationship by a cylindrical support member 15. The support member is fabricated of an insulating material, which is typically any suitable ceramic material. Over the support member is placed an outer coating of a variable valence oxide semiconductor 17, auch as stannous oxide, that has been prepared to provide for a porous structure whereby a maximized surface area is presented to the surrounding air. The outer surface is in electrical contact with both electrodes whereby an electrical current can be passed therethrough. A pair of leads 19,20 are also provided by which the detector can be placed within an appropriate circuit.

To provide for a porous outer coating, the semiconductor material is powdered by milling, grinding or the like and the powder intermixed with a material that is volatile at relatively low temperatures, such as stearic acid, wax, low melt resins or the like. The volatizing temperature should be below that at which molecular oxygen, as found in air, will combine with the stannous oxide to form stannic oxide. The mixture is then placed over the support member by any suitable means known in the art and the additive then volatized to create the desired porous structure.

Figure 2:
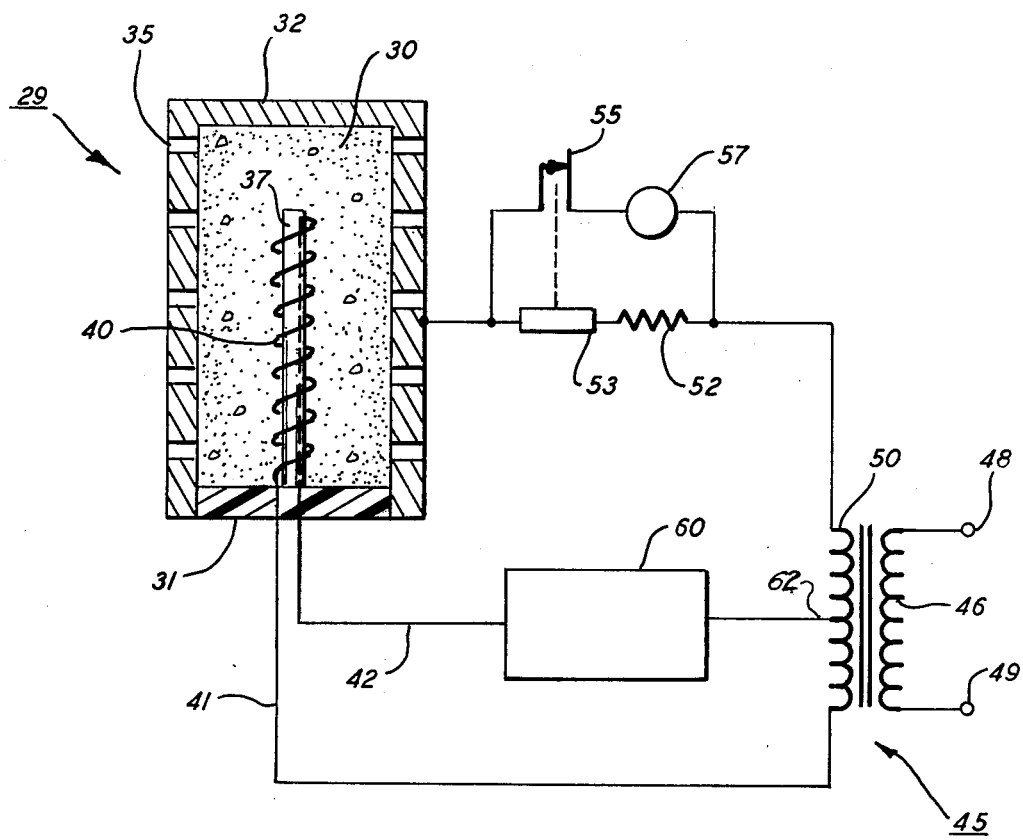
FIG. 2 is a plan view in section showing another embodiment of the invention which includes means for purging absorbed ozone from the detecting element.

FIG. 2 shows a second embodiment of the invention in which detector 29 includes a variable valence semiconductor that is dispersed within a block 30 also containing some inorganic materials such as clay, quartz particles, alumina and the like which will render the block porous. The block is seated upon an insulating base 31 and enclosed within a conductive housing 32. The housing is provided with a series of openings or holes 35 through which surrounding air can penetrate the housing to reach the porous sensing element 30.

A cylindrical support rod 37 is anchored in the base 31 and passes upwardly into the sensor element. A heating element or coil 40 is spiral wound about the rod with the terminal ends 41,42 of the heater being brought out of the element through the base.

In this embodiment, the housing 32 serves as one electrode of the detector while the heater coil serves as the second. Power to the detector is supplied by a transformer 45. The primary coil 46 of the transformer is connected to a suitable source of power at terminals 48,49. The secondary windings 50 are connected at the ends thereof to each of the electrodes thereby supplying a constant voltage over the detector circuit. Under normal operating conditions, when low levels of ozone are present in the surrounding air, a predictable amount of current is passed through the semiconductor element whereby a constant voltage is dropped over load resistor 52 and the relay 53 that is in series therewith. In practice, the relay is held energized by the flow of current thereby opening a normally closed contact 55 that is in series circuit relation with an alarm horn 57 of well known design.

In the case of an N-type oxide semiconductor, the conductivity of the element 30 will be quickly reduced in the presence of ozone thereby effecting the flow of current through the circuit. The relay, in response to the change in current, will be deenergized thus closing the contact 55 and setting off the alarm. A purge control circuit 60 of any suitable design is also placed in the heater circuit which can be manually or automatically activated to provide heater current to the coil 40. As illustrated, the heater coil is connected via control network 60 to a center tap 62 on the secondary windings of the transformer.

Sufficient energy is provided to the heater to raise the temperature of the element to a level, generally around 200° C., thereby releasing adsorbed oxygen and returning the associated valence electrons to the conduction band. Again, the purge cycle can be terminated after a period of time either manually or automatically so that the restored element may again sample the surrounding air.

While this invention has been described in reference to the disclosure above, it is not necessarily confined to the structure set forth above and the invention is broad enough to encompass any changes or modifications that might come within the scope of the following claims.

I claim:

1. A sensing element for detecting the presence of ozone at ambient temperatures and pressures including
   a porous body section containing a lower valence oxide of a variable valence semiconductor material that is capable of being oxidized in the presence of ozone to a higher valence oxide at ambient temperatures and pressures, and
   at least two electrodes mounted in spaced apart contact with the body section whereby an electrical current may be passed therethrough.

2. The sensing element of claim 1 wherein said body contains an admixture of a volatile material and the body is formed by volatizing said material.

3. The sensing element of claim 2 wherein said volatile material is organic and it volatizes at a temperature at which molecular oxygen combines with said lower valence oxide to form a higher valence oxide.

4. The sensing element of claim 1 further including a heater means in thermal contact with the body section for periodically raising the temperature of said body to purge adsorbed oxygen therefrom.

5. The sensing element of claim 1 wherein the oxide semiconductor is an N-type element whereby its conductivity is reduced in the presence of ozone.

6. The sensing element of claim 1 wherein the oxide semiconductor is a P-type element whereby its conductivity is increased in the presence of ozone.

7. The sensing device of claim 1 further including circuit means for producing a flow of current through said body section and an alarm means in said circuit for providing a signal when the flow of current through said body section changes.

8. A sensing element for detecting the presence of ozone in air including
   a porous sensing body formed of a stannous oxide semiconductor capable of dissociating ozone at ambient temperatures and pressures to form stannic oxide, and
   at least two electrodes in spaced apart contact with the body whereby a flow of electrical current may be passed therethrough.

9. The sensing element of claim 8 further including heater means in thermal contact with said body whereby the body section can be periodically purged.

10. The sensing element of claim 9 wherein said heater comprises one of said electrodes.

11. The sensing element of claim 8 wherein the sensing body is coated upon an insulating substrate.

12. The sensing element of claim 8 wherein said semiconductor is mixed with a porous insulating material.

* * * * *